(12) United States Patent
Prechtl et al.

(10) Patent No.: US 6,616,990 B2
(45) Date of Patent: Sep. 9, 2003

(54) CHIRAL 1, 3-DIOXANE COMPOUNDS

(75) Inventors: Frank Prechtl, Frankfurt (DE); Sylke Haremza, Neckargemuend (DE); Frank Meyer, Heidelberg (DE); Robert Parker, Mannheim (DE); Kathrin Kürschner, Mannheim (DE); Volkmar Vill, Hamburg (DE); Matthias Paul, Otzberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/809,144

(22) Filed: Mar. 16, 2001

(65) Prior Publication Data

US 2001/0030312 A1 Oct. 18, 2001

(30) Foreign Application Priority Data

Mar. 20, 2000 (DE) .......................... 100 13 507

(51) Int. Cl.$^7$ .................. C09K 19/58; C09K 19/52; C09K 19/34; C09K 19/20; C09K 19/12; C07D 319/06; C07D 239/02

(52) U.S. Cl. .............. 428/1.1; 252/299.01; 252/299.61; 252/299.64; 252/299.65; 252/299.66; 252/299.67; 544/298; 544/335; 549/369; 549/370

(58) Field of Search .................. 252/299.61, 299.66, 252/299.67, 299.64, 299.65, 299.5; 428/1.1; 549/369, 370; 544/335, 298

(56) References Cited

U.S. PATENT DOCUMENTS

| | | | |
|---|---|---|---|
| 3,325,439 A | 6/1967 | Steinbach et al. | |
| 5,518,653 A | 5/1996 | Buchecker et al. | 252/299.61 |
| 5,707,545 A | 1/1998 | Schlosser et al. | 252/299.61 |
| 5,798,147 A | 8/1998 | Beck et al. | |
| 5,833,880 A | 11/1998 | Siemensmeyer et al. | |
| 5,849,216 A | 12/1998 | Illian et al. | 252/299.61 |
| 5,942,030 A | 8/1999 | Schuhmacher et al. | |
| 6,136,225 A | 10/2000 | Meyer et al. | |
| 6,136,251 A | 10/2000 | Etzbach et al. | |
| 6,225,479 B1 | 5/2001 | Buchecker et al. | 549/370 |

FOREIGN PATENT DOCUMENTS

| | | |
|---|---|---|
| DE | 44 23 044 | 1/1996 |
| DE | 196 25 441 | 1/1998 |
| DE | 198 35 730 A1 | 2/1999 |
| DE | 197 45 647 A1 | 4/1999 |
| DE | 197 48 818 | 5/1999 |
| DE | 199 05 394 A1 | 8/2000 |
| EP | 0 457 105 | 11/1991 |
| EP | 0 541 081 | 5/1993 |
| EP | 0 684 246 | 11/1995 |
| EP | 0 774 452 | 5/1997 |
| EP | 0 782 995 | 7/1997 |
| GB | 877776 | 9/1961 |
| GB | 1017755 | 1/1966 |
| GB | 773890 | 5/1997 |
| GB | 2 328 436 | 2/1999 |
| WO | WO 93/13093 | 7/1993 |
| WO | WO 95/22586 | 8/1995 |
| WO | WO 95/24454 | 9/1995 |
| WO | WO 95/24455 | 9/1995 |
| WO | WO 95/04351 | 2/1996 |
| WO | WO 96/02597 | 2/1996 |
| WO | WO 96/24647 | 8/1996 |
| WO | WO 97/00600 | 1/1997 |
| WO | WO 97/27252 | 6/1997 |
| WO | WO 97/27251 | 7/1997 |
| WO | WO 97/34862 | 9/1997 |
| WO | WO 98/12265 | 3/1998 |
| WO | WO 98/47979 | 10/1998 |
| WO | WO 99/11733 | 3/1999 |

OTHER PUBLICATIONS

J. Szulc, et al., Liquid Crystals, vol. 14, No. 5, XP–000383398, pp. 1377–1387, "Three Ring Dioxanes as Dopants Enhancing the Stability of the Smectic C Phase", May 1993.

Primary Examiner—Shean C. Wu
(74) Attorney, Agent, or Firm—Oblon, Spivak, McClelland, Maier & Neustadt, P.C.

(57) ABSTRACT

The present invention relates to chiral 1,3-dioxane compounds and diastereomers thereof of the general formula I

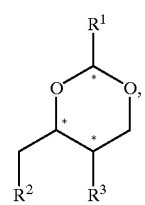

(I)

where $R^1$, $R^2$ and $R^3$ are as defined in the description, and the use of these compounds as chiral dopants for liquid-crystalline systems.

The invention further relates to non-polymerizable or polymerizable liquid-crystalline compositions comprising at least one chiral 1,3-dioxane compound of the formula (I) of the invention, the use of these non-polymerizable or polymerizable liquid-crystalline compositions for producing optical components, the use of the polymerizable liquid-crystalline compositions for printing or coating substrates, for preparing dispersions and emulsions, films or pigments and optical components, printed or coated substrates, dispersions and emulsions, films and pigments of this type.

18 Claims, No Drawings

CHIRAL 1, 3-DIOXANE COMPOUNDS

BACKGROUND OF THE INVENTION

(1) Field of the Invention

The present invention relates to chiral 1,3-dioxane compounds and diastereomers thereof, and to the use of these compounds as chiral dopants for liquid-crystalline systems.

(2) Description of the Preferred Embodiments

The invention further relates to non-polymerizable or polymerizable liquid-crystalline compositions comprising at least one chiral 1,3-dioxane compound of the invention, the use of these non-polymerizable or polymerizable liquid-crystalline compositions for producing optical components, the use of the polymerizable liquid-crystalline compositions for printing or coating substrates, for preparing dispersions and emulsions, films or pigments and optical components, printed or coated substrates, dispersions and emulsions, films and pigments of this type.

The preparation of cholesteric liquid-crystal mixtures usually involves using a liquid-crystalline (nematic) base material and one or more optically active dopants. This preparation method makes it possible to vary the optical properties of the mixture simply by changing the nematic compound/dopant ratio. However, to minimize possible negative effects of the dopant on the other properties of the nematic host system, such as phase behavior and phase range, there is a particular demand for dopants which, even when added in small amounts, cause large changes in optical properties.

Numerous chiral dopants for liquid-crystalline phases are known from the scientific and patent literature. It is all the more astonishing that chiral 1,3-dioxane compounds were apparently not considered previously as dopants for liquid-crystalline systems.

BRIEF SUMMARY OF THE INVENTION

It is an object of the present invention to provide additional chiral compounds which are suitable for preparing cholesteric liquid-crystalline compositions and have a relatively high twisting power and correspondingly exhibit great effects on the optical properties of the liquid-crystalline host system even in comparatively small amounts.

We have found that this object is achieved by a chiral compound of the general formula I

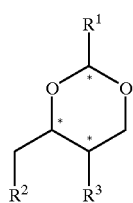

(I)

or a diastereomer thereof,
where
  $R^1$ is [P—$Y^1$—($A^1$)$_m$—$Y^2$—]$_q$M—$Y^3$—($A^2$)$_n$—$Y^4$— and
  $R^2$ and $R^3$ are each, independently of one another and independently of $R^1$, [P—$Y^1$—($A^1$)$_m$—$Y^2$—]$_q$M—$Y^3$—($A^2$)$_n$—$Y^{4'}$—,
where
  $A^1$ and $A^2$ are each a spacer having from one to 30 carbon atoms, M is a mesogenic group,
$Y^1$, $Y^2$, $Y^3$, $Y^4$ are each a chemical single bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—,
$Y^{4'}$ is —O—, —O—CO—, —O—CO—O— or —O—CO—N(R)—,
R is hydrogen or $C_1$-$C_4$-alkyl,
P is hydrogen, $C_1$-$C_{12}$-alkyl, a polymerizable group or a group suitable for polymerization or a radical having a polymerizable group or a group suitable for polymerization,
m and n are each 0 or 1, and
q is 1, 2 or 3,
where $A^1$, $A^2$, $Y^1$, $Y^2$, $Y^3$, $Y^4$, $Y^{4'}$, M and P and the indices m, n and q of $R^1$ to $R^3$ can be identical or different, and $R^2$ and $R^3$ are attached to the 1,3-dioxane skeleton via the oxygen atom of $Y^{4'}$, with the proviso that at least one of the radicals Y, in each case adjacent to A, is a chemical bond if one or both of the indices m and n is/are 0.

DETAILED DESCRIPTION OF THE PREFERRED EMBODIMENTS

Suitable spacers $A^1$ and $A^2$ are all groups known for this purpose to a person skilled in the art. The spacers usually contain one to 30, preferably one to 12, particularly preferably one to six, carbon atoms and consist of predominantly linear aliphatic groups. They may be interrupted in the chain, for example by non-adjacent oxygen or sulfur atoms or imino or alkylimino groups, for example methylimino groups. Suitable substituents for the spacer chain are fluorine, chlorine, bromine, cyano, methyl and ethyl.

Examples of representative spacers are:

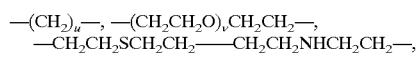

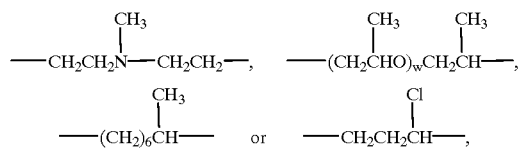

where u is 1 to 30, preferably 1 to 12, v is 1 to 14, preferably 1 to 5, and w is 1 to 9, preferably 1 to 3.

Preferred spacers are ethylene, propylene, n-butylene, n-pentylene and n-hexylene.

Particularly suitable mesogenic groups are those of the formula Ia
where
  T at each occurrence is a divalent, saturated or unsaturated carbocyclic or heterocyclic radical,
  $Y^5$ at each occurrence is a chemical single bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—, and
  r is 0, 1, 2 or 3, where, if r<0, T in each instance it occurs is identical or different and $Y^5$ in each instance it occurs is identical or different.

Note: The definition of the radical T as being divalent requires further explanation. It will be understood that this divalency only applies to the attachment of a radical T in question to the adjacent radical(s) T, one of the q moieties P—Y$^1$—(A$^1$)$_m$—Y$^2$— and/or —Y$^3$—(A$^2$)$_n$—Y$^4$— or —Y$^3$—(A$^2$)$_n$—Y$^{4'}$—, respectively.

For example, when two or three moieties P—Y$^1$—(A$^1$)$_m$—Y$^2$— (q equals two or three) are attached to the mesogenic group M, which as such has a valency of (q+1) according to its definition in formula I, the valency of at least one radical T in question obviously increases to three or possibly even four.

This may be illustrated by way of example for q equals 3 and r equals 3 for two of the possible isomers, i.e.

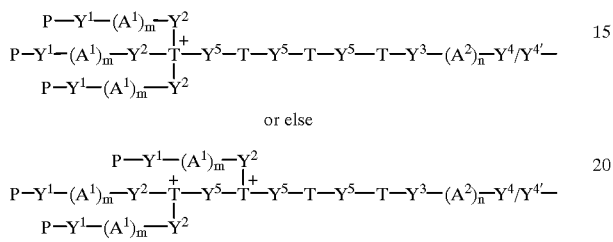

or else

In the former case, the radical T in question (marked with $^x$) is divalent in terms of attachment of one moiety P—Y$^1$—(A$^1$)$_m$—Y$^2$— and an adjacent radical T, but has a total valency of four, since it has two additional moieties P—Y$^1$—(A$^1$)$_m$—Y$^2$— attached to it. In the latter case, the two radicals T in question are divalent in terms of attachment of one moiety P—Y$^1$—(A$^1$)$_m$—Y$^2$— and one adjacent radical T or two adjacent radicals T, but the attachment of, in each case, one additional moiety P—Y$^1$—(A$^1$)$_m$—Y$^2$— results in a valency of three for the two radicals T in question.

Furthermore, here and throughout this application, at least one of the q moieties P—Y$^1$—(A$^1$)$_m$—Y$^2$— is attached terminally to the mesogenic group M as defined in the formulae I or Ia.

The radicals T may be ring systems which are substituted by fluorine, chlorine, bromine, cyano, hydroxyl, formyl, nitro, $C_1$–$C_{20}$-alkyl, $C_1$–$C_{20}$-alkoxy, $C_1$–$C_{20}$-alkoxycarbonyl, $C_1$–$C_{20}$-monoalkylaminocarbonyl, $C_1$–$C_{20}$-alkylcarbonyl, $C_1$–$C_{20}$-alkylcarbonyloxy or $C_1$–$C_{20}$-alkylcarbonylamino. Preferred radicals T are:

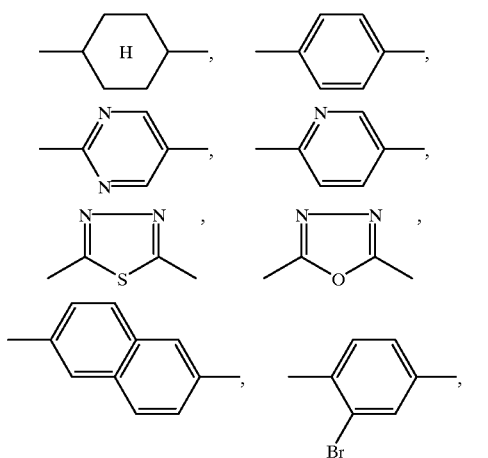

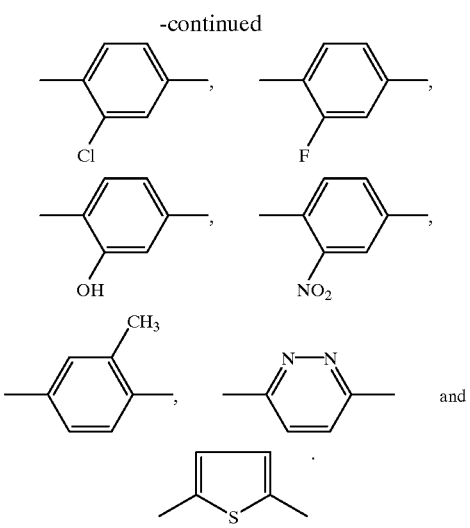

Examples of mesogenic groups M for R$^1$, R$^2$ and R$^3$ are:

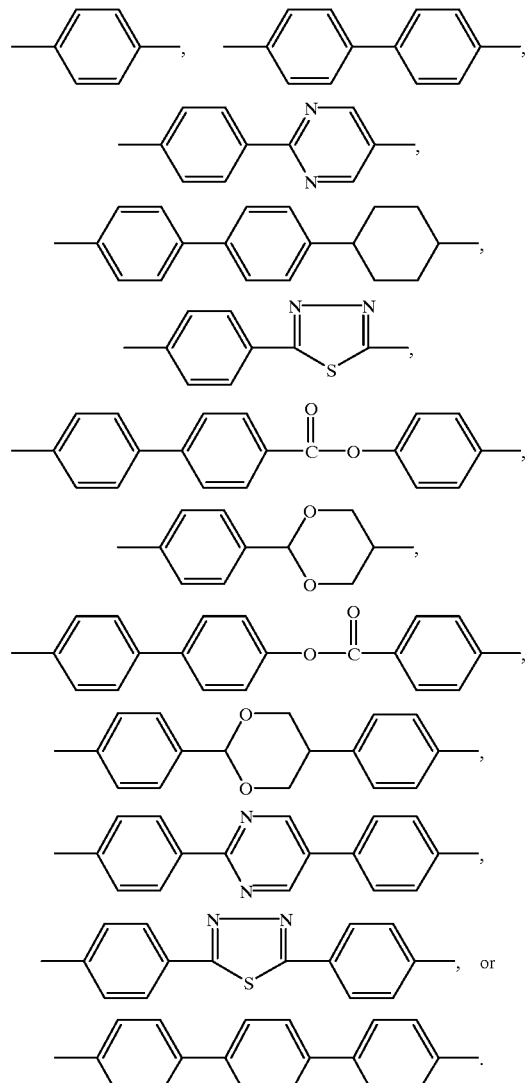

Further possible mesogenic groups M correspond to the following formulae:

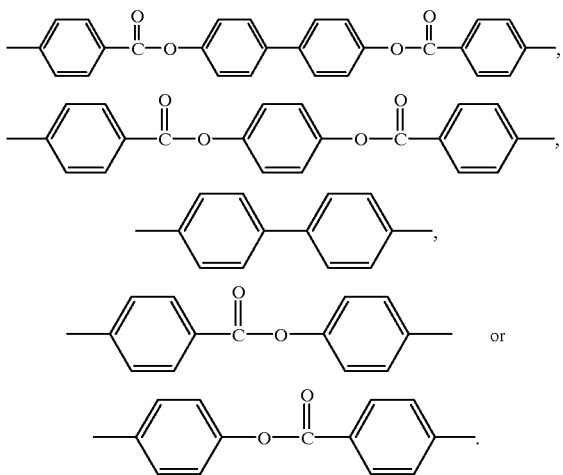

In accordance with the above examples for possible radicals T, the (unsubstituted) mesogenic groups shown above may of course be substituted by fluorine, chlorine, bromine, cyano, hydroxyl, formyl, nitro, $C_1$–$C_{20}$-alkyl, $C_1$–$C_{20}$-alkoxy, $C_1$–$C_{20}$-alkoxycarbonyl, $C_1$–$C_{20}$-monoalkylaminocarbonyl, $C_1$–$C_{20}$-alkylcarbonyl, $C_1$–$C_{20}$-alkylcarbonyloxy or $C_1$–$C_{20}$-alkylcarbonylamino. Preferred substituents are in particular short-chain aliphatic radicals, such as methyl, ethyl, n-propyl, i-propyl, n-butyl, i-butyl, sec-butyl, tert-butyl and alkoxy, alkoxycarbonyl, alkylcarbonyl, alkylcarbonyloxy, alkylcarbonylamino and monoalkylaminocarbonyl radicals which contain these alkyl groups.

Preferred 1,3-dioxane compounds are those in which, in the mesogenic group of the formula Ia, the index r is 0 for $R^1$ and the index r, independently at each occurrence, is 0 or 1 for $R^2$ and $R^3$. As mesogenic groups, mention may be made in particular of

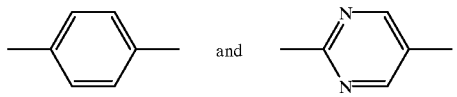

for $R^1$, and
for $R^2$ and $R^3$:

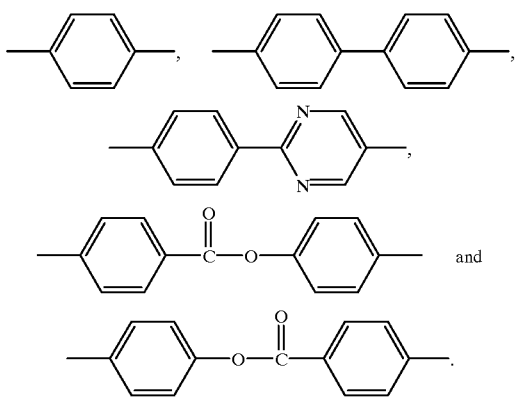

Furthermore, these mesogenic groups may be substituted, as mentioned above.

It is furthermore also possible to attach one or more of the mesogenic radicals M directly to the corresponding groups P without a spacer $A^1$. In these cases, the indices m or n are 0, and $Y^1/Y^2$ together are a chemical single bond.

$C_1$–$C_{12}$-Alkyl radicals for P are branched or unbranched $C_1$–$C_{12}$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, n-decyl, n-undecyl and n-dodecyl.

Preferred alkyl radicals for P are the branched or unbranched $C_1$–$C_6$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl and n-hexyl.

Polymerizable groups or groups suitable for polymerization or radicals having a polymerizable group or a group suitable for polymerization (such groups or radicals are hereinafter also simply called "reactive radicals") which are suitable for P are:

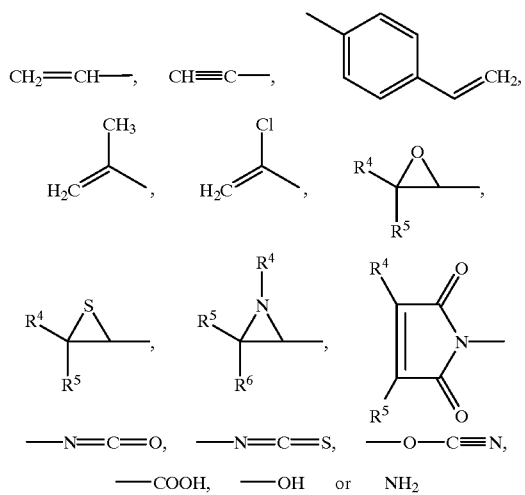

where $R^4$ to $R^6$ may be identical or different and are each hydrogen or $C_1$–$C_4$-alkyl, such as methyl, ethyl, n-propyl, isopropyl, n-butyl, isobutyl, sec-butyl or tert-butyl.

Of the polymerizable groups, the cyanates can spontaneously trimerize to cyanurates. The other groups mentioned require further compounds containing complementary reactive groups for polymerization. Thus, for example, isocyanates can polymerize with alcohols to give urethanes and with amines to give urea derivatives. Thiiranes and aziridines behave similarly. Carboxyl groups can be condensed to give polyesters and polyamides. The maleiimido group is particularly suitable for free-radical copolymerization with olefinic compounds, for example styrene, or compounds comprising styrene structural elements.

The complementary reactive radicals may, together with the corresponding reactive radicals, be present in a single 1,3-dioxane compound of the invention (so that this compound may potentially polymerize with itself) or in an additional 1,3-dioxane compound of the invention. Alternatively, these complementary reactive radicals may, together with the corresponding reactive radicals, be present in a single (auxiliary) compound or in further (auxiliary) compounds of this type.

Particularly suitable polymerizable groups are acrylate, methacrylate and vinyl.

Preference is also given to compounds of the formulae I, in which, in $R^1$, $P—Y^1—(A^1)_m—Y^2—$ is hydrogen, i.e. P is hydrogen, $Y^1$ and $Y^2$ are each a chemical single bond and m is 0, and m is not 0 in at least one $P—Y^1—(A^1)_m—Y^2—$ of $R^2$ and $R^3$. This preference means that at least one of the latter radicals has a group P which is attached to the mesogenic group M via spacer $A^1$ and $Y^1/Y^2$, and, in the case of $R^1$, $[P—Y^1—(A^1)_m—Y^2—]_qM—Y^3— —(A^2)_n—Y^4—$ is reduced to $[H—]_qM—Y^3—(A^2)_n—Y^4—$ or, taking formula Ia into account, to $[H—]_q(—T—Y^5)_r—T—Y^3—(A^2)_n—Y^4—$.

For the two exemplary cases mentioned above in the note, this gives

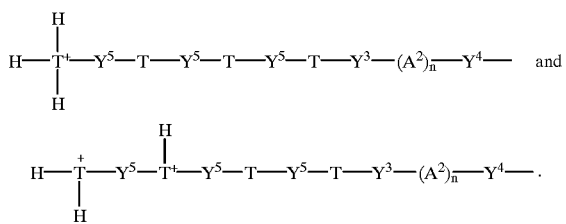

This is of course equivalent to the fact that the mesogenic group M in $R^1$ is no longer substituted with $P—Y^1—(A^1)_m—Y^2—$ moieties.

Preference is also given to compounds of the invention in which q is 1 in $R^2$ and $R^3$, i.e. each mesogenic group M of R2 and R3 is substituted only with a single $P—Y^1—(A^1)_m—Y^2—$ moiety which is then, in accordance with the remarks made in the above note, terminally attached to the mesogenic group M, and this, in accordance with the two above examples, leads to

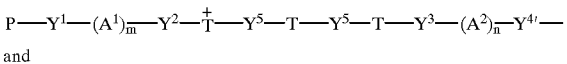
and
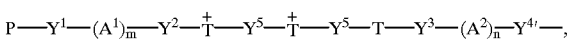

which is of course equivalent in this case.

Particularly preferred chiral compounds for the purposes of the present invention are based on the diastereomer of formula I',

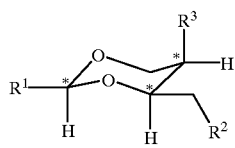

(I')

where $R^1$, $R^2$ and $R^3$ are as defined for formula I. The abovementioned preferences apply analogously to the compounds of the formula I'.

According to the invention, the compounds of the formula I and their preferred embodiments are used as chiral dopants for liquid-crystalline systems. The term "liquid-crystalline systems" as used herein is not limited to systems in which one or more constituents have liquid-crystalline properties per se (in the temperature range of interest) and are present in the system, but also includes those systems in which liquid-crystalline behavior is only achieved by mixing the components or by admixing the chiral compound(s) of the invention (e.g. lyotropic systems). It may furthermore be noted that the compounds of the invention do not necessarily have to exhibit liquid-crystalline behavior themselves.

The invention further provides liquid-crystalline and polymerizable liquid-crystalline compositions comprising at least one chiral compound of the formula I or a preferred embodiment.

Liquid-crystalline compositions for the purposes of the present invention are in particular non-polymerizable compositions which are not capable of forming polymerization or condensation products under conventional conditions. These compositions can be prepared, for example, by mixing one or more of the compounds of the invention with suitable commercially available liquid-crystalline materials as used, for example, for active LC layers in display technology. Accordingly, in the compounds of the invention, P in formula I is hydrogen or $C_1–C_{12}$-alkyl.

The invention provides the use of these (non-polymerizable) liquid-crystalline compositions for producing optical components, such as LCDs. The invention also provides optical components obtained in this way.

The present invention furthermore provides polymerizable liquid-crystalline compositions. These are in particular those compositions in which at least one of the components is capable of forming polymerization or condensation products under conventional conditions.

The desired degree of polymerization, crosslinking and/or condensation after polymerization or condensation is complete may be controlled depending on the number of reactive radicals in the components of these compositions. In such compositions, the compounds of the formula I of the invention have at least one, preferably two reactive radicals P, which are in particular attached to $R^2$ and $R^3$. These compositions are easily obtainable by mixing one or more of the compounds of the invention with suitable polymerizable, liquid-crystalline materials. Suitable polymerizable, liquid-crystalline compounds are described, for example, in WO 95/22586, 95/24454, 95/24455, 96/04351, 96/24647, 97/00600, 97/34862 and 98/47979 and German Offenlegungsschrift 198 35 730 and have essentially the schematic structure P—Y—A—Y—M—Y—A—Y—P, where P, Y, A and M have the same meanings as P, $Y^1$, to $Y^4$, $A^1$, $A^2$ and M in formula I.

The invention provides the use of these polymerizable liquid-crystalline compositions for producing optical components, such as polarizers or filters.

The present invention furthermore provides such optical components which have been obtained using these polymerizable liquid-crystalline compositions of the invention.

According to the invention, the claimed polymerizable liquid-crystalline compositions are used for printing or coating substrates. In this case, the compositions may contain further additives. Suitable additives include additives selected from the group consisting of photoinitiators, reactive thinners and diluents, additives selected from the group consisting of antifoams and deaerators, lubricants and flow auxiliaries, thermally curing or radiation-curing auxiliaries, substrate wetting auxiliaries, wetting and dispersion auxiliaries, hydrophobicizing agents, adhesion promoters and auxiliaries for improving the scratch resistance, additives selected from the group consisting of dyes and pigments and additives selected from the group consisting of light, heat and/or oxidation stabilizers.

The chemicophysical nature of these additives is described in detail in the prior German application 199 05 394.4. This publication furthermore describes liquid-crystalline compositions which fall into the same category as the polymerizable liquid-crystalline compositions of the invention, possibly in admixture with the abovementioned additives. Accordingly, as described in the prior German publication 199 05 394.4, the polymerizable liquid-crystalline compositions claimed in the present application, possibly in admixture with said additives, can be used as printing or coating compositions for substrates.

The present invention furthermore provides printed or coated substrates which have been produced using the polymerizable compositions of the invention, if desired in admixture with the abovementioned additives.

Examples of such substrates are paper and cardboard products, for example for carrier bags, magazines, brochures, gift wrappings and packaging materials for consumables, food products and luxury products, sheets, for example for decorative or non-decorative packaging, textiles of any kind and leather.

Other substrates are (consumer) electronic products, such as MC, MD, DVD and video recorders, televisions, radios, telephones/mobiles etc. and electronic data processing equipment, products from the leisure, sports, domestic and games sector, for example bicycles, children's vehicles, skis, snowboards and surfboards, in-line skates, roller skates and ice-skates and domestic appliances. Such substrates furthermore include writing utensils and spectacle frames, for example.

Other substrates are surfaces encountered in the construction sector, such as building walls or window panes. In the latter case, a functional effect may be desired in addition to a decorative effect. Thus, it is possible to produce multilayers on the window material whose individual layers have different chemicophysical properties. If, for example, individual layers of the polymerizable liquid-crystalline compositions with opposite twisting (by use of one enantiomer and its optical antipode as dopant according to the present invention) or individual layers of crosslinked cholesteric liquid-crystalline compositions with the same helical handedness but different pitch and thus different reflection properties (by using different concentrations of dopant according to the present invention) are employed, specific wavelengths or wavelength ranges of the light spectrum can be reflected in a controlled manner. In this way it is possible to provide a window coating which is IR or UV reflective. For this aspect of the compositions of the invention, in particular heat-insulating coatings, reference is made to German Offenlegungsschrift 197 45 647.

The present invention also provides the use of the polymerizable liquid-crystalline compositions of the invention for preparing dispersions and emulsions, which are preferably water-based. For the preparation of such dispersions and emulsions, reference is made to WO 96/02597 and WO 98/47979 which describe the preparation of dispersions and emulsions using liquid-crystalline materials.

Accordingly, the present invention provides such dispersions and emulsions which have been prepared using the polymerizable liquid-crystalline compositions of the invention. These dispersions and emulsions can likewise be used for printing and coating substrates as described above by way of example.

The present invention furthermore provides the use of the polymerizable liquid-crystalline compositions of the invention for producing films. For the purposes of the present invention, such films are in particular self-supporting layers as obtained by polymerizing the compositions. These films may be on substrates or backings such that films can easily be removed and transferred to other substrates or backings for permanent adhesion by appropriate measures. Such films can be used, for example, in film coating and laminating processes.

Accordingly, the present invention also provides such films which have been prepared using the polymerizable liquid-crystalline compositions of the invention.

The present invention furthermore provides the use of the polymerizable liquid-crystalline compositions of the invention for preparing pigments.

The preparation of such pigments is known and described in detail in WO 99/11733, for example. Furthermore, it is also possible to prepare pigments of predefined shape and size by using printing methods or by means of nets with gaps in which the polymerizable composition is placed. The liquid-crystalline composition is then polymerized or condensed followed by removal from the substrate or net. These procedures are described in detail in WO 96/02597, WO 97/27251, WO 97/27252 and EP 0 931 110.

The polymerizable liquid-crystalline compositions can be converted into polymers having a frozen liquid-crystalline order structure with the aid of their reactive groups and, depending on their chemical nature, by condensation or free-radical or ionic polymerization processes, which can be initiated by photochemical reactions.

These pigments may be single-layered (homogeneous) or multilayered. However, the latter pigments can usually only be obtained if coating processes are used in which a plurality of layers are formed successively on top of one another followed by a final mechanical comminution.

Accordingly, the present invention also provides pigments which have been prepared from such polymerizable liquid-crystalline compositions of the invention.

EXAMPLE 1a

Preparation of 4,6-O-benzylidene-D-galactopyranose

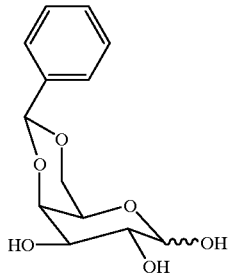

Composition: $C_{13}H_{16}O_6$ Molecular weight: 268.3 g/mol
Solid

A mixture of 10.0 g of D-galactose (55.5 mmol), 9.1 ml of benzaldehyde dimethyl acetal (61.0 mmol) and 12 mg of p-toluenesulfonic acid in 40 ml of dimethylformamide is stirred vigorously at 60° C., maintaining a constant pressure of 140 mbar to remove the methanol which forms. The galactose is completely dissolved after about 25 min. The reaction is terminated by cooling and addition of 0.3 ml of triethylamine. The reaction mixture is evaporated under reduced pressure and purified by column chromatography (eluent: ethyl acetate +0.1% by weight of triethylamine). Yield: 7.7 g (52% of theory)

EXAMPLE 1b

Preparation of 2,4-O-benzylidene-D-threose

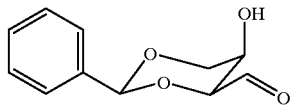

Composition: $C_{11}H_{12}O_4$ Molecular weight: 208.2 g/mol
Solid

A solution of 12.60 g of sodium metaperiodate (60 mmol) and 2.4 g of sodium hydrogencarbonate (30 mmol) in 200 ml of water are admixed with 6.7 g of 4,6-O-benzylidene-D-galactopyranose (25 mmol). After 0.5 h, the reaction mixture is evaporated under reduced pressure, the resulting residue is admixed with 200 ml of ethanol, again evaporated and extracted five times with 200 ml of warm ethyl acetate each time. The combined organic phases are washed with water, dried over sodium sulfate and then evaporated under reduced pressure. The resulting product is immediately used in the next stage. Yield: 3.56 g (68% of theory)

EXAMPLE 1c

Preparation of 2,4-O-benzylidene-D-threitol

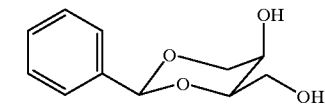

Composition: $C_{11}H_{14}O_4$ Molecular weight: 210.2 g/mol
Wax

A solution of 3.56 g of 2,4-O-benzylidene-D-threose (17.1 mmol) in 75 ml of ethanol is admixed with a solution of 726 mg of sodium borohydride (19.2 mmol) in 7.5 ml of water at room temperature. After 2 h, the solution is evaporated under reduced pressure, the residue is taken up in 100 ml of ethyl acetate, washed twice with 10 ml of 10% strength sodium sulfate solution, dried over sodium sulfate and then evaporated under reduced pressure. Yield: 3.06 g (85% of theory)

1H-NMR (400 MHz, $CDCl_3$): δ=7.51 (mc, 2H, $H_{Ar}$-2, $H_{Ar}$-6), 7.38 (mc, 3H, $H_{Ar}$-3, $H_{Ar}$-4, $H_{Ar}$-5), 5.60 (s, 1H, H-2), 4.22 (dd, 1H, H-6a), 4.07 (dd, 1H, H-6b), 4.02 (ddd, 1H, H-4), 3.92 (dd, 1H, $CH_AH_BOH$), 3.83 (dd, 1H, $CH_AH_BOH$), 3.68 (ddd, 1H, H-5). $3J_{H-4, H-5}$=1.3, $3J_{H-4, H-A}$=6.7, $3J_{H-4, H-B}$=5.2, $3J_{H-5, H-6a}$=1.7, $3J_{H-5, H-6b}$=1.3, $2J_{H-A, H-B}$=11.6, $2J_{H-6a, H-6b}$=12.0 Hz. 13C-NMR (100 MHz, $CDCl_3$): δ=137.52 ($C_{Ar}$-1), 129.24 ($C_{Ar}$-4), 128.48 ($C_{Ar}$-3, $C_{Ar}$-5), 126.02 ($C_{Ar}$-2, $C_{Ar}$-6), 101.57 (OCHO), 79.60 (C-4), 72.59 (C-6), 64.55 (C-5), 62.89 ($CH_2OH$).

EXAMPLE 2

Preparation of 4-hexoxybenzoyl-4'-oxybenzoic acid

Composition: $C_{20}H_{22}O_5$ Molecular weight: 342.4 g/mol
Phase behavior: K 165 N 235 I Solid A solution of 6.90 g of 4-hydroxybenzoic acid (50 mmol) in 100 ml of 1N sodium hydroxide solution is admixed with a solution of 11.1 ml of 4-hexyloxybenzoic chloride (50 mmol) in 50 ml of acetone at 0° C. with stirring. The milky solution is adjusted to pH 2–3 with 6N hydrochloric acid and filtered. The resulting solid is dissolved in dioxane and refluxed for 4 h. The solution is then evaporated under reduced pressure and the resulting residue is recrystallized from acetone. Yield: 3.08 g (18% of theory)

1H-NMR (400 MHz, $CDCl_3$): δ=8.20 (d, 2H, $H_{Ar}$-2', $H_{Ar}$-6'), 8.18 (d, 2H, $H_{Ar}$-2, $H_{Ar}$-6), 7.34 (d, 2H, $H_{Ar}$-3', $H_{Ar}$-5'), 6.98 (d, 2H, $H_{Ar}$-3, $H_{Ar}$-5), 4.05 (t, 2H, $OCH_2C_5H_{11}$), 1.83 (mc, 2H, $OCH_2CH_2C_4H_9$), 1.53–1.30

(m, 6H, 3xCH$_2$), 0.92 (t, 3H, CH$_3$). 3J$_{Ar}$=9.1, 3J$_{OCH2}$=6.6, 3J$_{CH2CH3}$=7.1 Hz. 13C-NMR (100 MHz, CDCl$_3$): δ=170.92 (COOH), 164.34, 163.83 (C$_{Ar}$-4, COO), 155.55 (C$_{Ar}$-4'), 132.43 (C$_{Ar}$-2', C$_{Ar}$-6'), 131.89 (C$_{Ar}$-2, C$_{Ar}$-6), 126.62 (C$_{Ar}$-1'), 122.01 (C$_{Ar}$-3', C$_{Ar}$-5'), 120.96 (C$_{Ar}$-1), 114.28 (C$_{Ar}$-3, C$_{Ar}$-5), 68.40 (OCH$_2$), 31.70, 29.47, 26.08, 23.01 (CH$_2$), 14.45 (CH$_3$).

EXAMPLE 3

Preparation of (2S,4R,5R)-4,5-di-O-(4-(p-hexyloxybenzoyloxy)benzoyl)-2-phenyl-1,3-dioxane

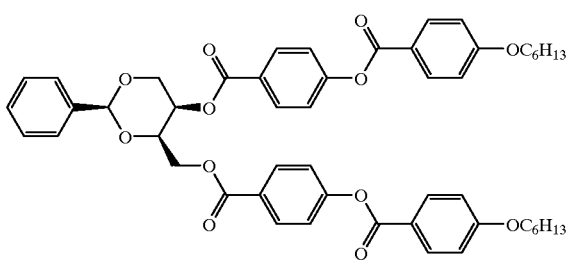

Composition: C$_{51}$H$_{54}$O$_{12}$, Molecular weight: 859.0 g/mol, Solid MALDI-TOF (m/z)=881 [MNa$^+$]Elemental analysis: calculated: C 71.31% by weight, H 6.34% by weight found: C 69.95% by weight, H 6.21% by weight
Phase behavior: K 123 I A solution of 4-hexyloxybenzoyl-4'-oxybenzoic acid (2 mmol), N,N'-dicyclohexylcarbodiimide (2.2 mmol), 2,4-O-benzylidene-D-threitol (1.1 mmol) and the catalyst 4-N,N-dimethylaminopyridine (4-DMAP; 0.1 mmol) in dichloromethane (5 ml) is stirred at room temperature until the reaction is complete. The N,N'-dicyclohexylurea which has formed is filtered off and the solvent is removed under reduced pressure. The residue is purified by column chromatography (eluent: petroleum ether 60/70: ethyl acetate 8:1) and recrystallized from ethanol. Yield: 0.48 g (56% of theory)

$^1$H-NMR (400 MHz, CDCl$_3$): δ=[8.23 (d, 2H), 8.13 (d, 2H), 8.12 (d, 2H), 8.09 (d, 2H), H$_{Ar}$-2, H$_{Ar}$-6, H$_{Ar}$-2', H$_{Ar}$-6', H$_{Ar}$-2'', H$_{ar}$-6'', H$_{Ar}$-2''', H$_{ar}$-6'''], 7.58 (mc, 2H, H$_{Bz}$-2, H$_{Bz}$-6), 7.41 (mc, 3H, H$_{Bz}$-3, H$_{Bz}$-4, H$_{Bz}$-5), [7.32 (d, 2H), 7.28 (d, 2H), H$_{Ar}$-3, H$_{Ar}$-5, H$_{Ar}$-3'', H$_{Ar}$-5''], 6.97 (mc, 4H, H$_{Ar}$-3', H$_{Ar}$-5', H$_{Ar}$-3 ''', H$_{ar}$-5'''), 5.73 (s, 1H, OCHO), 5.20 (ddd, 1H, H-5), 4.66 (dd, 1H, CH$_A$H$_B$OOC), 4.58 (ddd, 1H, H-4), 4.53 (dd, 1H, CH$_A$H$_B$OOC), 4.51 (dd, 1H, H-6a), 4.26 (dd, 1H, H-6b), 4.04 (t, 4H, OCH$_2$C$_5$H$_{11}$), 1.81 (mc, 4H, OCH$_2$CH$_2$C$_4$H$_9$), 1.53–1.30 (m, 12H, 6xCH$_2$), 0.92 (t, 6H, CH$_3$). $^3$J$_{Ar}$=9.1, $^3$J$_{H-4, H-5}$=1.5, $^3$J$_{H-4, Ha}$=6.2, $^3$J$_{H-4, Hb}$=5.6, $^3$J$_{H-5, H-6a}$=1.5, $^3$J$_{H-5, H-6b}$=1.5, $^2$J$_{Ha, Hb}$=10.7, $^2$J$_{H-6a, H-6b}$=13.2, $^3$J$_{OCH2}$=6.6 Hz. $^{13}$C-NMR (100 MHz, CDCl$_3$): δ=165.53, 165.39, 164.32, 164.31, 163.76 (4xCOO, C$_{Ar}$-4', C$_{Ar}$-4'''), 155.25, 155.06 (C$_{Ar}$-4, C$_{Ar}$-4''), 137.57 (C$_{Bz}$-1), 132.41, 132.38 (C$_{Ar}$-2', C$_{Ar}$-6', C$_{Ar}$-2''', C$_{Ar}$-6'''), 131.55, 131.35 (C$_{Ar}$-2, C$_{Ar}$-6, C$_{Ar}$-2'', C$_{Ar}$-6''), 129.26 (C$_{Bz}$-4), 128.39 (C$_{Bz}$-3, C$_{Bz}$-5), 126.98, 126.97 (C$_{Ar}$-1, C$_{Ar}$-1''), 126.22 (C$_{Bz}$-2, C$_{Bz}$-6), 122.03, 121.93 (C$_{Ar}$-3, C$_{Ar}$-5, C$_{Ar}$-3'', C$_{Ar}$-5'') 121.02, 121.00 (C$_{Ar}$-1', C$_{Ar}$-1'''), 114.38 (C$_{Ar}$-3', C$_{Ar}$-5', C$_{Ar}$-3''', C$_{Ar}$-5'''), 101.39 (C-2), 75.61 (C-4), 69.37 (C-6), 68.36 (OCH$_2$), 65.87 (C-5), 63.40 (CH$_2$OOC), 31.54, 29.04, 25.64, 22.58 (CH$_2$), 14.02 (CH$_3$).

EXAMPLE 4

Preparation of (2S,4R,5R)-4,5-di-O-(4-(acryloxybutyloxycarbonyloxy)benzoyl)-2-phenyl-1, 3-dioxane Solid

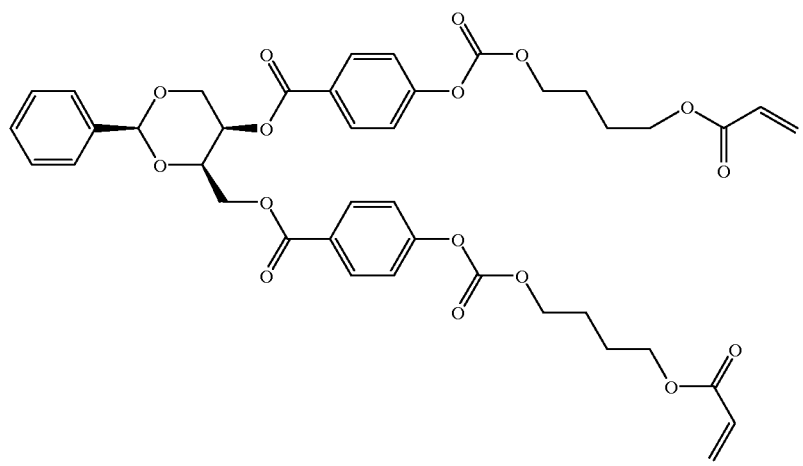

A solution of 4-(acryloxybutyloxycarbonyloxy)benzoic acid (2 mmol), N,N'-dicyclohexylcarbodiimide (2.2 mmol), 2,4-O-benzylidene-D-threitol (1.1 mmol; cf. Example 1c) and the catalyst 4-DMAP (0.1 mmol) in dichloromethane (5 ml) is stirred at room temperature until the reaction is complete, the N,N'-dicyclohexylurea which has been formed is filtered off and the solvent is removed under reduced pressure. The residue is finally purified by column chromatography and recrystallized from ethanol.

EXAMPLE 7

Preparation of Crosslinked Cholesteric Films

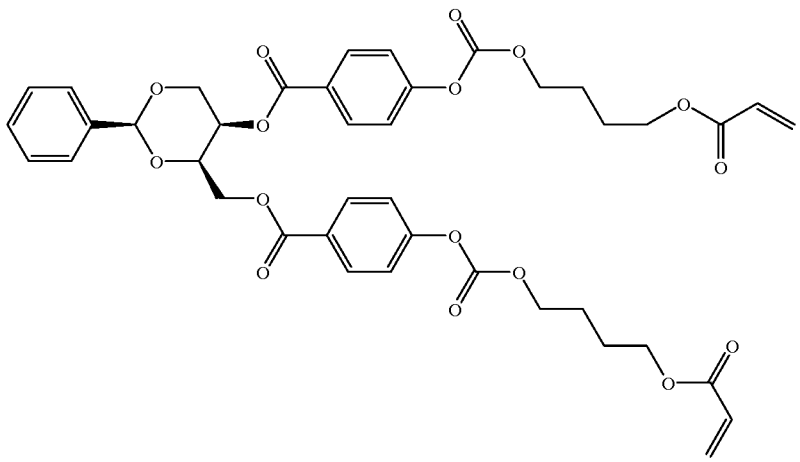

Dopant

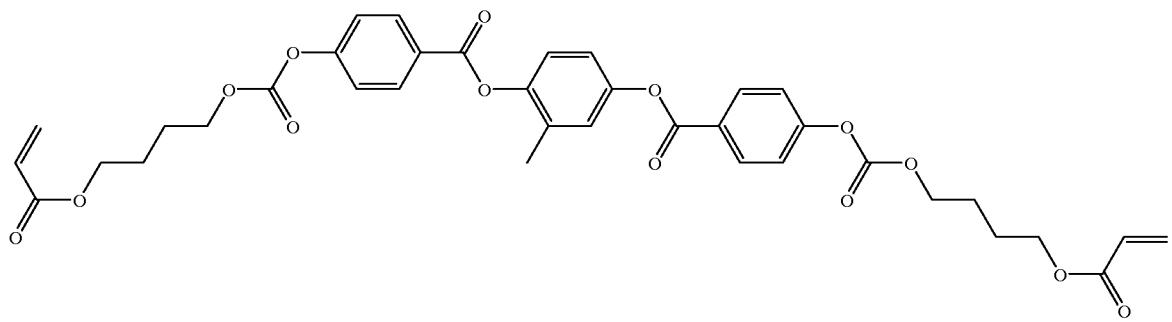

Liquid-crystalline host compound

A cholesteric mixture is prepared which comprises the compounds shown as chiral dopant and liquid-crystalline host compound. The undiluted cholesteric mixture comprises 94.2% by weight of the nematic host compound, 5.8% by weight of the chiral dopant and 2% by weight, based on the cholesteric mixture, of 1-hydroxycyclohexyl phenyl ketone photoinitiator which is available under the tradename Irgacure 184 (from Ciba). The mixture has a reflection maximum at a wavelength of $\lambda_{max}$=352 nm.

A film is prepared by dissolving this mixture in methyl ethyl ketone and knife-coating the solution as a thin layer onto a polyethylene terephthalate sheet. The layer has a wet film thickness of about 3 µm. The solvent is evaporated at 75° C., and the layer is cured by UV irradiation. The resulting polymerized or crosslinked cholesteric layer can be detached mechanically from the substrate. If desired, the resulting flakes can be comminuted to the desired size by conventional grinding methods and used as pigments, for example.

We claim:
1. A chiral compound of the general formula I

(I)

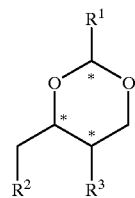

or a diastereomer thereof, where $R^1$ is $[P-Y^1-(A^1)_m-Y^2-]_qM-Y^3-(A^2)_n-Y^4-$, and $R^2$ and $R^3$ are each, independently of one another and independently of $R^1$, $[P-Y^1-(A^1)_m-Y^2-]_qM-Y^3-(A^2)_n-Y^{4'}-$, where $A^1$ and $A^2$ are each a spacer having from one to 30 carbon atoms, M is a mesogenic group, $Y^1$, $Y^2$, $Y^3$ and $Y^4$ are each a chemical single bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—, $Y^{4'}$ is —O—, —O—CO—, —O—CO—O— or —O—CO—N(R)—, R is hydrogen or $C_1$–$C_4$-alkyl, P is hydrogen, $C_1$–$C_{12}$-alkyl, a polymerizable group or a group suitable for polymerization or a radical having a polymerizable group or a group suitable for polymerization, m and n are each 0 or 1, and q is 1, 2 or 3, where $A^1$, $A^2$, $Y^1$, $Y^2$, $Y^3$, $Y^4$, $Y^{4'}$, M and P and the indices m, n and q of $R^1$ to $R^3$ can be identical or different, and $R^2$ and $R^3$ are attached to the 1,3-dioxane skeleton via the oxygen atom of $Y^{4'}$, with the proviso that at least one of the radicals Y, in each case adjacent to A, is a chemical bond if one or both of the indices m and n is/are 0.

2. A compound as claimed in claim 1, where the mesogenic group M has the formula Ia:

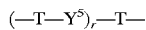

where

T at each occurrence is a divalent, saturated or unsaturated carbocyclic or heterocyclic radical, $Y^5$ at each occurrence is a chemical single bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—, and r is 0, 1, 2 or 3, where, if r>0, T in each instance it occurs is identical or different and $Y^5$ in each instance it occurs is identical or different.

3. A compound as claimed in claim 2, where, in the mesogenic group of the formula Ia, the index r is 0 for $R^1$ and the index r, independently at each occurrence, is 0 or 1 for $R^2$ and $R^3$.

4. A compound as claimed in claim 2 or 3, where T is selected from the group consisting of

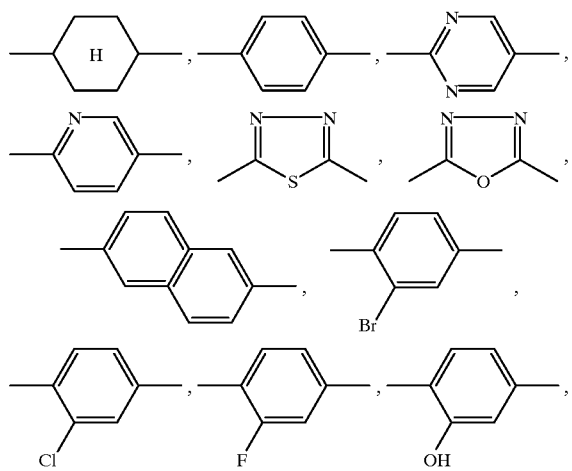

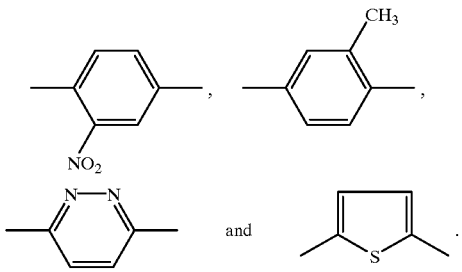

5. A compound as claimed in claim 1, wherein, in $R^1$, [P—$Y^1$—($A^1$)$_m$—$Y^2$—] is hydrogen and, in $R^2$ and $R^3$, m is not 0 in at least one P—$Y^1$—($A^1$)$_m$—$Y^2$—.

6. A compound as claimed in claim 1, wherein q is 1 in $R^2$ and $R^3$.

7. A method of doping liquid-crystalline systems, comprising:

doping a liquid-crystalline system with the chiral compound of claim 1.

8. A liquid-crystalline composition, comprising:

at least one chiral compound of claim 1.

9. A polymerizable liquid-crystalline composition, comprising:

at least one chiral compound of claim 1.

10. A method of producing optical components, comprising:

preparing an optical component from the composition of claim 8.

11. A method of producing optical components, comprising:

preparing an optical component from the polymerizable composition of claim 9.

12. An optical component prepared from the liquid-crystalline composition of claim 8.

13. An optical component prepared from the polymerizable liquid-crystalline composition of claim 9.

14. A method of printing or coating a substrate, comprising:

printing or coating a substrate with the composition of claim 9.

15. A method of preparing a dispersion or emulsion, comprising:

incorporating the composition of claim 9 into the dispersion or emulsion.

16. A method of producing a film, comprising:

forming a film with the composition of claim 9.

17. A method of preparing a pigment, comprising: incorporating the composition of claim 9 into a pigment formulation.

18. A printed or coated substrate, dispersion or emulsion, film or pigment prepared from the composition of claim 9.

* * * * *

UNITED STATES PATENT AND TRADEMARK OFFICE
CERTIFICATE OF CORRECTION

PATENT NO.   : 6,616,990 B2
DATED        : September 9, 2003
INVENTOR(S)  : Prechtl et al.

It is certified that error appears in the above-identified patent and that said Letters Patent is hereby corrected as shown below:

<u>Title page,</u>
Item [*] Notice, should read
-- [*]   Notice: Subject to any disclaimer, the term of this patent is extended or adjusted under 35 U.S.C. 154(b) by 11 days. --

Signed and Sealed this

Ninth Day of March, 2004

JON W. DUDAS
*Acting Director of the United States Patent and Trademark Office*